(12) United States Patent
Svendsen

(10) Patent No.: US 6,218,170 B1
(45) Date of Patent: Apr. 17, 2001

(54) LACCASE MUTANTS

(75) Inventor: Allan Svendsen, Birkerød (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/518,901

(22) Filed: Mar. 6, 2000

Related U.S. Application Data

(62) Division of application No. 09/028,887, filed on Feb. 24, 1998, now Pat. No. 6,060,442.

(30) Foreign Application Priority Data

Feb. 28, 1997 (DK) .................................................... 0221/97

(51) Int. Cl.[7] .............................. C12N 1/20; C12N 9/02; C12N 15/00; C07H 21/04; C07K 1/00
(52) U.S. Cl. .................. 435/252.3; 435/189; 435/320.1; 435/254.3; 536/23.2; 530/350
(58) Field of Search ......................... 536/23.2; 435/189, 435/252.3, 320.1, 254.3; 530/350

(56) References Cited

U.S. PATENT DOCUMENTS 5,770,419  6/1998  Feng et al. ........................ 435/189
5,856,164  1/1999  Outtrup et al. ..................... 435/202

FOREIGN PATENT DOCUMENTS

WO 95/11296   4/1995  (WO) .
WO 95/33836  12/1995  (WO) .
WO 97/09431   3/1997  (WO) .
WO 95/33837  12/1997  (WO) .

OTHER PUBLICATIONS

Germann et al., (1988) The Journal of Biological Chemistry, 2:885–896.

Xu et al., (1996) Biochimica et Biophysica Acta 1292: 303–311.

Kojima et al., (1990) The Journal of Biological Chemistry, 265(25):15224–15230.

*Primary Examiner*—Tekchand Saidha
(74) *Attorney, Agent, or Firm*—Elias J. Lambiris, Esq.; Reza Green, Esq.

(57) ABSTRACT

The present invention relates to laccase mutants with increased oxidation potential and/or changed pH optimum and/or altered mediator pathway and/or altered $O_2/OH^-$ pathway.

16 Claims, No Drawings

LACCASE MUTANTS

CROSS-REFERENCE TO RELATED APPLICATIONS

This application is a divisional of U.S. application Ser. No. 09/028,887 filed Feb. 24, 1998 now U.S. Pat. No. 6,060,442 and claims priority under 35 U.S.C. 119 of Danish application 0221/97 filed Feb. 28, 1997, the contents of which are fully incorporated herein by reference.

FIELD OF THE INVENTION

The present invention relates to laccase mutants with increased oxidation potential and/or changed pH optimum and/or altered mediator pathway and/or altered $O_2/OH^-$ pathway.

BACKGROUND OF THE INVENTION

Laccase is a polyphenol oxidase (EC 1.10.3.2) which catalyses the oxidation of a variety of inorganic and aromatic compounds, particularly phenols, with the concomitant reduction of molecular oxygen to water.

Laccase belongs to a family of blue copper-containing oxidases which includes ascorbate oxidase and the mammalian plasma protein ceruloplasmin. All these enzymes are multi-copper-containing proteins.

Because laccases are able to catalyze the oxidation of a variety of inorganic and aromatic compounds, laccases have been suggested in many potential industrial applications such as lignin modification, paper strengthening, dye transfer inhibition in detergents, phenol polymerization, hair colouring, and waste water treatment.

The various applications ask for laccases with specific properties. It is the purpose of the present application to create laccase variants with increased oxidation potential and/or changed pH optimum and/or altered mediator pathway and/or altered $O_2/OH^-$-pathway.

BRIEF DISCLOSURE OF THE INVENTION

The present invention relates to laccase variants, in particular to

A variant of a parent laccase, which variant has laccase activity, and increased oxidation potential and comprises a mutation in a position corresponding to at least one of the following positions:
G511A,V,P,L,I,F,Y,W;
T428A,V,P,L,I,F,Y,W;
S510A,V,P,L,I,F,Y,W;
D106A,V,P,L,I,F,Y,W;
N109A,V,P,L,I,F,Y,W,Q;
L500I,F,Y,W;
A108V,P,L,I,F,Y,W;
G514A,V,P,L,I,F,Y,W;
wherein the parent laccase has the amino acid sequence given in SEQ ID No. 1 or the parent laccase has an amino acid sequence which is at least 80% homologous to SEQ ID No. 1;

A variant of a parent laccase, which variant has laccase activity and an altered pH optimum and comprises a mutation in a position corresponding to at least one of the following positions:
192–193;
234–236;
269;
293–294;
364–365;
372–373;
426–433;
503–513;
wherein the parent laccase has the amino acid sequence given in SEQ ID No. 1 or the parent laccase has an amino acid sequence which is at least 80% homologous to SEQ ID No. 1;

A variant of a parent laccase, which variant has laccase activity and an altered mediator efficiency and comprises a mutation in a position corresponding to at least one of the following positions:
185–194;
235;
293–294;
365–373;
427–429;
505;
507–508;
510–511;
wherein the parent laccase has the amino acid sequence given in SEQ ID No. 1 or the parent laccase has an amino acid sequence which is at least 80% homologous to SEQ ID No. 1; and A variant of a parent laccase, which variant has laccase activity and an altered $O_2/OH^-$-pathway and comprises a mutation in a position corresponding to at least one of the following positions:
A506E;
N109D;
H93E;
H95E;
M433E;
M480E;
wherein the parent laccase has the amino acid sequence given in SEQ ID No. 1 or the parent laccase has an amino acid sequence which is at least 80% homologous to SEQ ID No. 1.

In still further aspects the invention relates to DNA encoding such variants and methods of preparing the variants.

Finally, the invention relates to the use of the variants for various industrial purposes.

DETAILED DISCLOSURE OF THE INVENTION

Homologous Laccases

A number of laccases produced by different fungi are homologous on the amino acid level. For instance, when using the homology percent obtained from UWGCG program using the GAP program with the default parameters (penalties: gap weight=3.0, length weight=0.1; WISCONSIN PACKAGE Version 8.1-UNIX, August 1995, Genetics Computer Group, 575 Science Drive, Madison, Wis., USA 53711) the following homology was found: *Myceliophthora thermophila* laccase comprising the amino acid sequence shown in SEQ ID No. 1: 100%; *Scytalidium thermophilum* laccase comprising the amino acid sequence shown in SEQ ID No. 2: 81.2%.

Because of the homology found between the above mentioned laccases, they are considered to belong to the same class of laccases, namely the class of "Myceliophthora-like laccases".

Accordingly, in the present context, the term "Myceliophthora-like laccase" is intended to indicate a laccase which, on the amino acid level, displays a homology of at least 80% to the Myceliophthora laccase SEQ ID NO 1, or a laccase which, on the amino acid level, displays a homology of at least 85% to the Myceliophthora laccase SEQ ID NO 1, or a laccase which, on the amino acid level, displays a homology of at least 90% to the Myceliophthora laccase SEQ ID NO 1, or a laccase which, on the amino acid level, displays a homology of at least 95% to the Myceliophthora laccase SEQ ID NO 1, or a laccase which, on the amino acid level, displays a homology of at least 98% to the Myceliophthora laccase SEQ ID NO 1.

In the present context, "derived from" is intended not only to indicate a laccase produced or producible by a strain of the organism in question, but also a laccase encoded by a DNA sequence isolated from such strain and produced in a host organism containing said DNA sequence. Finally, the term is intended to indicate a laccase which is encoded by a DNA sequence of synthetic and/or cDNA origin and which has the identifying characteristics of the laccase in question.

Variants with Altered Oxidation Potential

The redox potentials of various wild type laccases have been found to be the following (measured at pH 5.3): $E°$, V vs NHE
*Myceliophthora thermophila* (SEQ ID No. 1): 0.48
*Scytalidium thermophilum* (SEQ ID No. 2): 0.53

It is contemplated that it is possible to increase the oxidation potential of a parent laccase, wherein said variant is the result of a mutation, i.e. one or more amino acid residues have been deleted from, replaced or added to the parent laccase. Preferred positions for mutations are the following:
*Myceliophthora thermophila* laccase (SEQ ID No. 1):
G511A,V,P,L,I,F,Y,W;
T428A,V,P,L,I,F,Y,W;
S510A,V,P,L,I,F,Y,W;
D106A,V,P,L,I,F,Y,W;
N109A,V,P,L,I,F,Y,W,Q;
L500I,F,Y,W;
A108V,P,L,I,F,Y,W;
G514A,V,P,L,I,F,Y,W; in particular
G511A,V,L,I,F;
T428V;
S510V;
D106L;
N109I,F,Q;
L500F;
A108V,I;
G514A,V,L,I,F.

Preferred variants include any combination of the above mentioned mutations.

Variants with Altered pH Optimum

The desired pH optimum of a laccase depends on which application is of interest, e.g., if the laccase is to be used for denim bleaching the preferred pH optimum will be around pH 5–8, whereas if the laccase is to be used for washing purposes; the preferred pH optimum will be around pH 8–10.

It is contemplated that it is possible to alter the pH optimum of a parent laccase wherein said variant is the result of a mutation, i.e. one or more amino acid residues have been deleted from, replaced or added to the parent laccase. Preferred positions for mutations are the following:
*Myceliophthora thermophila* (SEQ ID No. 1):
192–193;
234–236;
269;
293–294;
364–365;
372–373;
426–433;
503–513.
Preferred substitutions are the following: E, D, L, I, F, Y, W.

Variants with Altered Mediator Efficiency

Laccases are often used in combination with so called mediators or enhancers, e.g., in combination with phenothiazine or phenothiazine related compounds (see WO 95/01426) or in combination with acetosyringone or acetosyringone related compounds (see WO 96/10079).

It is contemplated that it is possible to alter the mediator efficiency (in order to make the mediator more efficient), of a parent laccase wherein said variant is the result of a mutation, i.e. one or more amino acid residues have been deleted from, replaced or added to the parent laccase. Preferred positions for mutations are the following:
*Myceliophthora thermophila* laccase (SEQ ID No. 1):
185–194;
235;
293–294;
365–373;
427–429;
505;
507–508;
510–511.
Preferred substitutions are in particular one or more of the following mutations:
N189G,A,S,T;
S190G,A;
F371* (deletion);
F371G,A.

Variants with Altered $O_2/OH^-$-pathway

It is contemplated that it is possible to lower the possibility of $OH^-$ entering the trinuclear Cu site by producing one or more of the following mutations:
*Myceliophthora thermophila* (SEQ ID No. 1):
A506E;
N109D;
H93E;
H95E;
M433E;
M480E.

Methods of Preparing Laccase Variants

Several methods for introducing mutations into genes are known in the art. After a brief discussion of the cloning of laccase-encoding DNA sequences, methods for generating mutations at specific sites within the laccase-encoding sequence will be discussed.

Cloning a DNA Sequence Encoding a Laccase

The DNA sequence encoding a parent laccase may be isolated from any cell or microorganism producing the laccase in question, using various methods well known in the art. First, a genomic DNA and/or cDNA library should be constructed using chromosomal DNA or messenger RNA from the organism that produces the laccase to be studied. Then, if the amino acid sequence of the laccase is known, homologous, labelled oligonucleotide probes may be synthesized and used to identify laccase-encoding clones from a genomic library prepared from the organism in question. Alternatively, a labelled oligonucleotide probe containing sequences homologous to a known laccase gene could be used as a probe to identify laccase-encoding clones, using hybridization and washing conditions of lower stringency.

A method for identifying laccase-encoding clones involves inserting cDNA into an expression vector, such as a plasmid, transforming laccase-negative fungi with the resulting cDNA library, and then plating the transformed fungi onto agar containing a substrate for laccase, thereby allowing clones expressing the laccase to be identified.

Alternatively, the DNA sequence encoding the enzyme may be prepared synthetically by established standard methods, e.g. the phosphoroamidite method. In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers.

Site-directed Mutagenesis

Once a laccase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the laccase-encoding sequence, is created in a vector carrying the laccase gene. Then the synthetic nucleotide, bearing the desired mutation, is annealed to a homologous portion of the single-stranded DNA. The remaining gap is then filled in with T7 DNA polymerase and the construct is ligated using T4 ligase. A specific example of this method is described in Morinaga et al. (1984). U.S. Pat No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method of introducing mutations into laccase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

The random mutagenesis of a DNA sequence encoding a parent laccase may conveniently be performed by use of any method known in the art.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents.

The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the laccase enzyme by any published technique, using e.g. PCR, LCR or any DNA polymerase and ligase.

When PCR-generated mutagenesis is used, either a chemically treated or non-treated gene encoding a parent laccase enzyme is subjected to PCR under conditions that increase the misincorporation of nucleotides (Deshler 1992; Leung et al., Technique, Vol.1, 1989, pp. 11–15).

A mutator strain of *E. coli* (Fowler et al., Molec. Gen. Genet., 133, 1974, pp. 179–191), *S. cereviseae* or any other microbial organism may be used for the random mutagenesis of the DNA encoding the laccase enzyme by e.g. transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or cDNA library prepared from an organism expressing the parent laccase enzyme. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to the expression step or the screening step being performed. Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenizing agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are fungal hosts such as *Aspergillus niger* or *Aspergillus oryzae*.

The mutated DNA sequence may further comprise a DNA sequence encoding functions permitting expression of the mutated DNA sequence.

Localized Random Mutagenesis

The random mutagenesis may advantageously be localized to a part of the parent laccase in question. This may, e.g., be advantageous when certain regions of the enzyme have been identified to be of particular importance for a given property of the enzyme, and when modified are expected to result in a variant having improved properties.

Such regions may normally be identified when the tertiary structure of the parent enzyme has been elucidated and related to the function of the enzyme.

The localized random mutagenesis is conveniently performed by use of PCR-generated mutagenesis techniques as described above or any other suitable technique known in the art.

Alternatively, the DNA sequence encoding the part of the DNA sequence to be modified may be isolated, e.g. by being inserted into a suitable vector, and said part may subsequently be subjected to mutagenesis by use of any of the mutagenesis methods discussed above.

With respect to the screening step in the above-mentioned method of the invention, this may conveniently be performed by use of aa filter assay based on the following principle:

A microorganism capable of expressing the mutated laccase enzyme of interest is incubated on a suitable medium and under suitable conditions for the enzyme to be secreted, the medium being provided with a double filter comprising a first protein-binding filter and on top of that a second filter exhibiting a low protein binding capability. The microorganism is located on the second filter. Subsequent to the incubation, the first filter comprising enzymes secreted from the microorganisms is separated from the second filter comprising the microorganisms. The first filter is subjected to screening for the desired enzymatic activity and the corresponding microbial colonies present on the second filter are identified.

The filter used for binding the enzymatic activity may be any protein binding filter e.g. nylon or nitrocellulose. The top filter carrying the colonies of the expression organism may be any filter that has no or low affinity for binding proteins e.g. cellulose acetate or Durapore™. The filter may be pretreated with any of the conditions to be used for screening or may be treated during the detection of enzymatic activity.

The enzymatic activity may be detected by a dye, fluorescence, precipitation, pH indicator, IR-absorbance or any other known technique for detection of enzymatic activity.

The detecting compound may be immobilized by any immobilizing agent, e.g., agarose, agar, gelatine, polyacrylamide, starch, filter paper, cloth; or any combination of immobilizing agents.

Laccase Activity

In the context of this invention, the laccase activity was measured using 10-(2-hydroxyethyl)-phenoxazine (HEPO) as substrate for the various laccases. HEPO was synthesized using the same procedure as described for 10-(2-hydroxyethyl)-phenothiazine, (G. Cauquil in Bulletin de la Society Chemique de France, 1960, p. 1049). In the presence of oxygen laccases (E.C. 1.10.3.2) oxidize HEPO to a HEPO radical that can be monitored photometrically at 528 nm.

The *Myceliophthora thermophila* laccase was measured using 0.4 mM HEPO in 25 mM Tris-HCl, pH 7.5, 0.05% TWEEN-20 at 30° C. The absorbance at 528 nm was followed for 200 s and the rate calculated from the linear part of the progress curve.

Expression of Laccase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding a laccase variant of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding a laccase variant of the invention, especially in a fungal host, are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the laccase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene, the product of which complements a defect in the host cell, such as one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding a laccase variant, the promoter, terminator and other elements, respectively, and to insert them into suitable vectors containing the information necessary for replication, are well known to persons skilled in the art (cf., for instance, Sambrook et al. (1989)).

The cell of the invention, either comprising a DNA construct or an expression vector of the invention as defined above, is advantageously used as a host cell in the recombinant production of a laccase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a fungal cell.

The filamentous fungus may advantageously belong to a species of Aspergillus, e.g. *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing a laccase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the laccase variant of the invention. Suitable media are available from commercial suppliers or may be prepared according to published recipes (e.g. as described in catalogues of the American Type Culture Collection).

The laccase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Industrial Applications

The laccase variants of this invention possesses valuable properties allowing for various industrial applications, in particular lignin modification, paper strengthening, dye transfer inhibition in detergents, phenol polymerization, hair dyeing, textile dyeing, bleaching of textiles (in particular bleaching of denim as described in WO 96/12845 and WO 96/12846) and waste water treatment.

What is claimed is:

1. A DNA construct comprising a DNA sequence encoding a variant of a parent laccase, wherein said variant has laccase activity and increased oxidation potential relative to said parent and comprises a mutation in a position corresponding to at least one of the following positions in SEQ ID NO:1:

D106A,V,P,L,I,F,Y,W;
N109A,V,P,L,I,F,Y,W,Q;

wherein the parent laccase has the amino acid sequence given in SEQ ID No. 1 or the parent laccase has an amino acid sequence which is at least 80% homologous to SEQ ID No. 1, wherein said homology is determined using GAP with a GAP weight of 3.0 and a length weight of 0.1.

2. A recombinant expression vector comprising a DNA construct according to claim 1.

3. A cell comprising a vector according to claim 2.

4. A cell according to claim 3, wherein said cell is a microbial cell.

5. A cell according to claim 4, wherein said cell is a bacterium or a fungus.

6. A cell according to claim 5, wherein said cell is an *Aspergillus niger* or an *Aspergillus oryzae* cell.

7. A DNA construct comprising a DNA sequence encoding a variant of a parent laccase, wherein said variant has laccase activity and an altered pH optimum relative to said parent and comprises a mutation in a position corresponding to at least one of the following positions in SEQ ID NO:1:

185–194;
234–236;
269;
293–294;

wherein the parent laccase has the amino acid sequence given in SEQ ID No. 1 or the parent laccase has an amino acid sequence which is at least 80% homologous to SEQ ID No. 1, wherein said homology is determined using GAP with a GAP weight of 3.0 and a length weight of 0.1.

8. A recombinant expression vector comprising a DNA construct according to claim 7.

9. A cell comprising a vector according to claim 8.

10. A cell according to claim 9, wherein said cell is a microbial cell.

11. A cell according to claim 10, wherein said cell is an *Aspergillus niger* or an *Aspergillus oryzae* cell.

12. A DNA construct comprising a DNA sequence encoding a variant of a parent laccase, wherein said variant has laccase activity and an altered pH optimum relative to said parent and comprises a mutation in a position corresponding to at least one of the following positions in SEQ ID NO:1:

N109D;
H93E;
H95E;
M480E
wherein the parent laccase has the amino acid sequence given in SEQ ID No. 1 or the parent laccase has an amino acid sequence which is at least 80% homologous to SEQ ID No. 1, wherein said homology is determined using GAP with a GAP weight of 3.0 and a length weight of 0.1.

13. A recombinant expression vector comprising a DNA construct according to claim 12.

14. A cell comprising a vector according to claim 13.

15. A cell according to claim 14, wherein said cell is a microbial cell.

16. A cell according to claim 15, wherein said cell is an *Aspergillus niger* or an *Aspergillus oryzae cell.*

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 573 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Gln Gln Ser Cys Asn Thr Pro Ser Asn Arg Ala Cys Trp Thr Asp Gly
 1               5                  10                  15

Tyr Asp Ile Asn Thr Asp Tyr Glu Val Asp Ser Pro Asp Thr Gly Val
                20                  25                  30

Val Arg Pro Tyr Thr Leu Thr Leu Thr Glu Val Asp Asn Trp Thr Gly
            35                  40                  45

Pro Asp Gly Val Val Lys Glu Lys Val Met Leu Val Asn Asn Ser Ile
        50                  55                  60

Ile Gly Pro Thr Ile Phe Ala Asp Trp Gly Asp Thr Ile Gln Val Thr
65                  70                  75                  80

Val Ile Asn Asn Leu Glu Thr Asn Gly Thr Ser Ile His Trp His Gly
                85                  90                  95

Leu His Gln Lys Gly Thr Asn Leu His Asp Gly Ala Asn Gly Ile Thr
            100                 105                 110

Glu Cys Pro Ile Pro Pro Lys Gly Arg Lys Val Tyr Arg Phe Lys
        115                 120                 125

Ala Gln Gln Tyr Gly Thr Ser Trp Tyr His Ser His Phe Ser Ala Gln
        130                 135                 140

Tyr Gly Asn Gly Val Val Gly Ala Ile Gln Ile Asn Gly Pro Ala Ser
145                 150                 155                 160

Leu Pro Tyr Asp Thr Asp Leu Gly Val Phe Pro Ile Ser Asp Tyr Tyr
                165                 170                 175
```

```
Tyr Ser Ser Ala Asp Glu Leu Val Glu Leu Thr Lys Asn Ser Gly Ala
            180                 185                 190

Pro Phe Ser Asp Asn Val Leu Phe Asn Gly Thr Ala Lys His Pro Glu
            195                 200                 205

Thr Gly Glu Gly Glu Tyr Ala Asn Val Thr Leu Thr Pro Gly Arg Arg
            210                 215                 220

His Arg Leu Arg Leu Ile Asn Thr Ser Val Glu Asn His Phe Gln Val
225                 230                 235                 240

Ser Leu Val Asn His Thr Met Cys Ile Ile Ala Ala Asp Met Val Pro
                245                 250                 255

Val Asn Ala Met Thr Val Asp Ser Leu Phe Leu Gly Val Gly Gln Arg
                260                 265                 270

Tyr Asp Val Val Ile Glu Ala Asn Arg Thr Pro Gly Asn Tyr Trp Phe
        275                 280                 285

Asn Val Thr Phe Gly Gly Leu Leu Cys Gly Gly Ser Arg Asn Pro
        290                 295                 300

Tyr Pro Ala Ala Ile Phe His Tyr Ala Gly Ala Pro Gly Gly Pro Pro
305                 310                 315                 320

Thr Asp Glu Gly Lys Ala Pro Val Asp His Asn Cys Leu Asp Leu Pro
                325                 330                 335

Asn Leu Lys Pro Val Val Ala Arg Asp Val Pro Leu Ser Gly Phe Ala
                340                 345                 350

Lys Arg Ala Asp Asn Thr Leu Asp Val Thr Leu Asp Thr Thr Gly Thr
                355                 360                 365

Pro Leu Phe Val Trp Lys Val Asn Gly Ser Ala Ile Asn Ile Asp Trp
        370                 375                 380

Gly Arg Ala Val Val Asp Tyr Val Leu Thr Gln Asn Thr Ser Phe Pro
385                 390                 395                 400

Pro Gly Tyr Asn Ile Val Glu Val Asn Gly Ala Asp Gln Trp Ser Tyr
                405                 410                 415

Trp Leu Ile Glu Asn Asp Pro Gly Ala Pro Phe Thr Leu Pro His Pro
                420                 425                 430

Met His Leu His Gly His Asp Phe Tyr Val Leu Gly Arg Ser Pro Asp
        435                 440                 445

Glu Ser Pro Ala Ser Asn Glu Arg His Val Phe Asp Pro Ala Arg Asp
        450                 455                 460

Ala Gly Leu Leu Ser Gly Ala Asn Pro Val Arg Arg Asp Val Ser Met
465                 470                 475                 480

Leu Pro Ala Phe Gly Trp Val Val Leu Ser Phe Arg Ala Asp Asn Pro
                485                 490                 495

Gly Ala Trp Leu Phe His Cys His Ile Ala Trp His Val Ser Gly Gly
                500                 505                 510

Leu Gly Val Val Tyr Leu Glu Arg Ala Asp Asp Leu Arg Gly Ala Val
            515                 520                 525

Ser Asp Ala Asp Ala Asp Asp Leu Asp Arg Leu Cys Ala Asp Trp Arg
            530                 535                 540

Arg Tyr Trp Pro Thr Asn Pro Tyr Pro Lys Ser Asp Ser Gly Leu Lys
545                 550                 555                 560

His Arg Trp Val Glu Glu Gly Glu Trp Leu Val Lys Ala
                565                 570
```

(2) INFORMATION FOR SEQ ID NO: 2:

```
    (i) SEQUENCE CHARACTERISTICS:
        (A) LENGTH: 616 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 2:

Met Lys Arg Phe Phe Ile Asn Ser Leu Leu Leu Ala Gly Leu Leu
1               5                   10                  15

Asn Ser Gly Ala Leu Ala Ala Pro Ser Thr His Pro Arg Ser Asn Pro
            20                  25                  30

Asp Ile Leu Leu Glu Arg Asp Asp His Ser Leu Thr Ser Arg Gln Gly
            35                  40                  45

Ser Cys His Ser Pro Ser Asn Arg Ala Cys Trp Cys Ser Gly Phe Asp
50                      55                  60

Ile Asn Thr Asp Tyr Glu Thr Lys Thr Pro Asn Thr Gly Val Val Arg
65                  70                  75                  80

Arg Tyr Thr Phe Asp Ile Thr Glu Val Asp Asn Arg Pro Gly Pro Asp
                85                  90                  95

Gly Val Ile Lys Glu Lys Leu Met Leu Ile Asn Asp Lys Leu Leu Gly
            100                 105                 110

Pro Thr Val Phe Ala Asn Trp Gly Asp Thr Ile Glu Val Thr Val Asn
            115                 120                 125

Asn His Leu Arg Thr Asn Gly Thr Ser Ile His Trp His Gly Leu His
        130                 135                 140

Gln Lys Gly Thr Asn Tyr His Asp Gly Ala Asn Gly Val Thr Glu Cys
145                 150                 155                 160

Pro Ile Pro Pro Gly Gly Ser Arg Val Tyr Ser Phe Arg Ala Arg Gln
                165                 170                 175

Tyr Gly Thr Ser Trp Tyr His Ser Phe Ser Ala Gln Tyr Gly Asn
                180                 185                 190

Gly Val Ser Gly Ala Ile Gln Ile Asn Gly Pro Ala Ser Leu Pro Tyr
            195                 200                 205

Asp Ile Asp Leu Gly Val Leu Pro Leu Xaa Asp Trp Tyr Tyr Lys Ser
210                 215                 220

Ala Asp Gln Leu Val Ile Glu Thr Leu Xaa Lys Gly Asn Ala Pro Phe
225                 230                 235                 240

Ser Asp Asn Val Leu Ile Asn Gly Thr Ala Lys His Pro Thr Thr Gly
                245                 250                 255

Glu Gly Glu Tyr Ala Ile Val Lys Leu Thr Pro Asp Lys Arg His Arg
            260                 265                 270

Leu Arg Leu Ile Asn Met Ser Val Glu Asn His Phe Gln Val Ser Leu
        275                 280                 285

Ala Lys His Thr Met Thr Val Ile Ala Ala Asp Met Val Pro Val Asn
290                 295                 300

Ala Met Thr Val Asp Ser Leu Phe Met Val Gly Gln Arg Tyr Asp
305                 310                 315                 320

Val Thr Ile Asp Ala Ser Gln Ala Val Gly Asn Tyr Trp Phe Asn Ile
                325                 330                 335

Thr Phe Gly Gly Gln Gln Lys Cys Gly Phe Ser His Asn Pro Ala Pro
            340                 345                 350

Ala Ala Ile Phe Arg Tyr Glu Gly Ala Pro Asp Ala Leu Pro Thr Asp
        355                 360                 365
```

```
-continued

Pro Gly Ala Ala Pro Lys Asp His Gln Cys Leu Asp Thr Leu Asp Leu
    370             375             380

Ser Pro Val Val Gln Lys Asn Val Pro Val Asp Gly Phe Val Lys Glu
385             390             395                     400

Pro Gly Asn Thr Leu Pro Val Thr Leu His Val Asp Gln Ala Ala Ala
            405             410                 415

Pro His Val Phe Thr Trp Lys Ile Asn Gly Ser Ala Ala Asp Val Asp
            420             425             430

Trp Asp Arg Pro Val Leu Glu Tyr Val Met Asn Asn Asp Leu Ser Ser
        435             440             445

Ile Pro Val Lys Asn Asn Ile Val Arg Val Asp Gly Val Asn Glu Trp
        450             455             460

Thr Tyr Trp Leu Val Glu Asn Asp Pro Glu Gly Arg Leu Ser Leu Pro
465             470             475                     480

His Pro Met His Leu His Gly His Asp Phe Phe Val Leu Gly Arg Ser
            485             490                 495

Pro Asp Val Ser Pro Asp Ser Glu Thr Arg Phe Val Phe Asp Pro Ala
            500             505             510

Val Asp Leu Pro Arg Leu Arg Gly His Asn Pro Val Arg Arg Asp Val
        515             520             525

Thr Met Leu Pro Ala Arg Gly Trp Leu Leu Leu Ala Phe Arg Thr Asp
        530             535             540

Asn Pro Gly Ala Trp Leu Phe His Cys His Ile Ala Xaa His Val Ser
545             550             555                     560

Gly Gly Leu Ser Val Asp Phe Leu Glu Arg Pro Asp Glu Leu Arg Gly
            565             570             575

Gln Leu Thr Gly Glu Ser Lys Ala Glu Leu Glu Arg Val Cys Arg Glu
            580             585             590

Trp Lys Asp Trp Glu Ala Lys Ser Pro His Gly Lys Ile Asp Ser Gly
        595             600             605

Leu Lys Gln Arg Arg Trp Asp Ala
    610             615
```